United States Patent

Bauer et al.

[11] Patent Number: 5,902,884
[45] Date of Patent: May 11, 1999

[54] PROCESS FOR PREPARING N-ALKYLCARBAZOLES

[75] Inventors: Wolfgang Bauer, Maintal; Klaus Delpy, Dietzenbach; Gert Nagl, Niedredorfelden; Leonhard Unverdorben, Nidderau, all of Germany

[73] Assignee: Clariant GmbH, Frankfurt, Germany

[21] Appl. No.: 09/021,981

[22] Filed: Feb. 11, 1998

[30] Foreign Application Priority Data

Feb. 13, 1997 [DE] Germany ............ 197 05 466

[51] Int. Cl.$^6$ ............ C07D 209/86; C07D 209/82; C07D 209/88
[52] U.S. Cl. ............ 548/447; 548/440; 548/445
[58] Field of Search ............ 548/447, 440, 548/445

[56] References Cited

U.S. PATENT DOCUMENTS

| | | | |
|---|---|---|---|
| 2,783,237 | 2/1957 | Cavillito et al. | 260/293 |
| 5,254,700 | 10/1993 | Kamitamari et al. | 548/440 |
| 5,393,894 | 2/1995 | Becherer et al. | 548/445 |

FOREIGN PATENT DOCUMENTS

| | | |
|---|---|---|
| 0 557 993 A1 | 9/1993 | European Pat. Off. . |
| 4324707 | 8/1994 | Germany . |
| 342961 | 1/1960 | Switzerland . |

OTHER PUBLICATIONS

Zhang et al., CA 123:32903, 1995.
Polaczek et al., CA 123:202033, 1995.
LaVoie et al., CA 96:212264, 1982.
Chen et al., CA 102:72054, 1985.
Chakrabarty et al., CA 121:35243, 1994.
Bull. Chem. Soc. JPN., 54, 1897–1898 (1981).
Ullmann's Enzyklopadie der Technischen Chemie, 3rd edition, vol. 5, p. 80 and 4th edition, vol. 9, p. 120, 1954.
W. Herbst and K. Hunger, "Industrielle Pigmente," VCH Weinheim pp. 521–527, 1987.
Houben–Weyl, Methoden der Organischen Chemie, vol. E 6a (1994), pp. 975–976.
J. Heterocycl. Chem. 18, 315 (1981).
Liebigs Ann. Chem. 1987, 509.
Tetrahedron 46, 6113 (1990), No. 7.
BIOS Final Report 968, p. 197, Year Not Available.
Bull. Chem. Soc. Jpn. 54, 1897 (1981).
Bull. Chem. Soc. Jpn. 56, 280 (1983).
Derwent Abstract DE–A 4324707 (US equivalent 5,,393, 894), Feb. 5, 1996.

Primary Examiner—Laura L. Stockton
Attorney, Agent, or Firm—Susan S. Jackson

[57] ABSTRACT

Process for preparing N-alkylcarbazoles

The present invention relates to a process for preparing N-alkylcarbazoles of the formula I

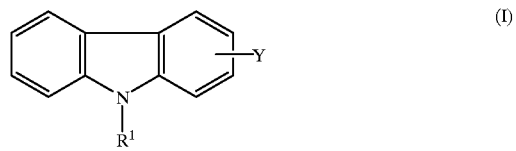

(I)

where $R^1$ is $(C_1–C_6)$-alkyl and

Y is hydrogen, $(C_1–C_6)$-alkyl, $(C_1–C_6)$-alkoxy, nitro or halogen, by reacting a carbazole of the formula II

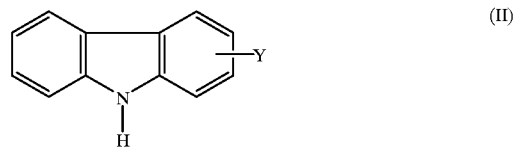

(II)

with an alkyl halide of the formula III $R^1$-X (III)

where X is a halogen atom,
in an inert solvent in the presence of an inorganic base and a catalyst of the formula IV $R^2R^3N-(CH_2)_n-NR^4R^5$ (IV)

where n is an integer from 2 to 8, $R^2$, $R^3$ and $R^4$ are, independently of one another, hydrogen or $(C_1–C_4)$-alkyl and $R^5$ is hydrogen, $(C_1–C_4)$-alkyl, amino-$(C_1–C_4)$-alkyl or N,N-di$(C_1–C_4)$-alkylamino-$(C_1–C_4)$-alkyl.

14 Claims, No Drawings

PROCESS FOR PREPARING N-ALKYLCARBAZOLES

The present invention relates to a process for preparing N-alkyl-carbazoles by reacting carbazoles with alkyl halides in the presence of a catalyst.

N-Alkylcarbazoles, in particular N-ethylcarbazole, are important intermediates for producing valuable dyes and pigments (see, for example, Ullmann's Enzyklopädie der Technischen Chemie, 3rd edition, volume 5, page 80 and 4th edition, volume 9, page 120; W. Herbst and K. Hunger, "Industrielle Pigmente", VCH Weinheim, pp. 521–527, 1987).

The introduction of an N-alkyl group into carbazole is carried out, for example, by alkylation of carbazole or carbazolides using alkyl halides, dialkyl sulfates and also alkyl arenesulfonates (see, for example, Houben-Weyl, Methoden der Organischen Chemie, Volume E 6a (1994), pp.975–976).

Other alkylating agents which can be used are diethyl N-(o-tolyl)phosphoramidate (J. Heterocycl. Chem. 18, 315 (1981)), dialkoxycarbenium tetrafluoroborates (Liebigs Ann. Chem. 1987, 509), diethyl carbonate (DE-A 4324707) and also diethyl oxalate (Tetrahedron 46, 6113 (1990)).

The use of dialkyl sulfates or alkyl arenesulfonates has the disadvantage that, owing to the toxic and carcinogenic properties of these compounds, costly measures have to be undertaken for ecological and occupational hygiene reasons.

When using diethyl N-(o-tolyl)phosphoramidate or dialkoxycarbenium tetrafluoroborates, the yields obtained are only 30% or 67% of the theoretical yield of N-ethylcarbazole. The formation and the disposal of the resulting by-products cause considerable economic and environmental disadvantages.

When using diethyl carbonate as alkylating agent in the presence of basic catalysts, very high temperatures of from 170° C. to 240° C. and long reaction times of up to 24 hours are required to achieve yields of >90% of the theoretical yield of N-ethylcarbazole. Thus, this process has an uneconomically high energy consumption and an unfavorable space/time yield.

N-Ethylcarbazole is prepared industrially by reacting carbazole with potassium hydroxide and ethylating the intermediate potassium carbazolide with ethyl chloride (see, for example, BIOS Final Report 968, p. 197). In this process too, long reaction times and high reaction temperatures lead to economic disadvantages.

To remedy these disadvantages, a series of catalysts have been used in alkylation reactions of carbazole or alkali metal carbazolides. However, in the ethylation of carbazole with ethyl bromide in a two-phase mixture of benzene and 50% strength aqueous sodium hydroxide solution in the presence of benzyltriethylammonium chloride as phase transfer catalyst, only 86.2% of the theoretical yield of N-ethylcarbazole is achieved (Bull. Chem. Soc. Jpn. 54, 1897 (1981)).

If polyethylene glycol dialkyl ethers are used as phase transfer catalysts in the reaction of carbazole with ethyl bromide in the two-phase mixture benzene/potassium hydroxide, these catalysts have to be used in equimolar amounts in order to achieve N-ethylcarbazole yields of 92% of theory (Bull. Chem. Soc. Jpn. 56, 280(1983)).

In these cases, it is necessary to use the particularly reactive ethyl bromide as alkylating agent or an equimolar amount of phase transfer catalyst, which makes these processes, also, uneconomical and ecologically disadvantageous. EP-A 557993 describes a process for preparing N-alkylcarbazoles in which carbazole is reacted with ethyl chloride in a two-phase system comprising, for example, 1,2-dichlorobenzene and 48% strength aqueous sodium hydroxide solution using trialkylamines as catalysts. At reaction times of 9 hours and reaction temperatures of 100° C., yields of far above 90% of the theoretical yield of N-ethylcarbazole are achieved. However, an industrial disadvantage of this process is that the catalyst used has to be removed from the organic product phase first obtained in the alkylation by means of an additional scrubbing process with aqueous sulfuric acid.

It has now surprisingly been found that the use of certain catalysts enables the abovementioned disadvantages, in particular those of the process described in EP-A 557993, to be avoided.

The present invention provides a process for preparing N-alkylcarbazoles of the formula I

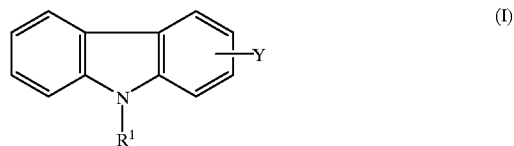

where
R$^1$ is (C$_1$–C$_6$)-alkyl and
Y is hydrogen, (C$_1$–C$_6$)-alkyl, (C$_1$–C$_6$)-alkoxy, nitro or halogen, by reacting a carbazole of the formula II

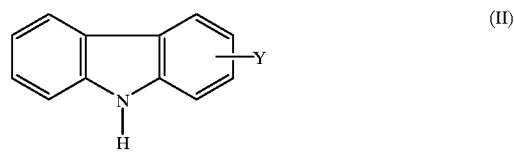

with an alkyl halide of the formula III

R$^1$–X                    III where X is a halogen atom,
in an inert solvent in the presence of an inorganic base and a catalyst of the formula IV

R$^2$R$^3$N–(CH$_2$)$_n$–NR$^4$R$^5$                    IV where
n is an integer from 2 to 8,
R$^2$, R$^3$ and R$^4$ are, independently of one another, hydrogen or (C$_1$–C$_4$)-alkyl and
R$^5$ is hydrogen, (C$_1$–C$_4$)-alkyl, amino-(C$_1$–C$_4$)-alkyl or N,N-di(C$_1$–C$_4$)-alkylamino-(C$_1$–C$_4$)-alkyl.

Alkyl groups can be linear or branched. (C$_1$–C$_6$)-alkyl as R$^1$ is, for example, methyl, ethyl, propyl, n-butyl, i-butyl, sec-butyl, tert-butyl, pentyl or hexyl. The same applies to the alkyl group in alkoxy as Y' and to (C$_1$–C$_4$)-alkyl, amino-(C$_1$–C$_4$)-alkyl or N,N-di(C$_1$–C$_4$)-alkylamino-(C$_1$–C$_4$)-alkyl as R$^2$, R$^3$, R$^4$ or R$^5$. A halogen atom as Y or X can be, for example, fluorine, chlorine, bromine or iodine.

In preferred compounds of the formula I, R$^1$ is (C$_1$–C$_4$)-alkyl, particularly preferably methyl or ethyl, and Y is hydrogen.

Alkyl halides of the formula III are preferably alkyl iodides, bromides or chlorides. Particular preference is given to alkyl chlorides. For example, it is possible to use methyl chloride, methyl bromide, methyl iodide, ethyl chloride, ethyl bromide, n-propyl chloride, n-propyl bromide, iso-butyl chloride, iso-butyl bromide, n-pentyl chloride or n-hexyl chloride. Very particular preference is given to ethyl chloride. The alkyl halides of the formula III are-preferably used in amounts of from 1.0 to 1.8 mol, particularly preferably from 1.1 to 1.5 mol per mole of carbazole of the formula I.

In the process of the invention, inorganic bases used can be, in particular alkali metal alkoxides and hydroxides, oxides, carbonates and also tertiary phosphates of the alkali metals and alkaline earth metals or mixtures thereof. Examples are sodium methoxide, sodium ethoxide, potassium tert-butoxide, lithium hydroxide, sodium hydroxide, potassium hydroxide, sodium carbonate, potassium carbonate, trisodium phosphate, calcium oxide, calcium hydroxide and barium hydroxide. Preferred inorganic bases are lithium hydroxide, sodium hydroxide and potassium hydroxide, particularly preferably sodium hydroxide and potassium hydroxide. Alkali metal hydroxides are very particularly preferably used in the form of concentrated, in particular from 40 to 60% strength, aqueous solutions. The inorganic bases are preferably used in amounts of from 0.9 to 3.0 eq, particularly preferably from 1.1 to 2.0 eq, per mole of carbazole of the formula 1.

Inert solvents which can be used in the process of the invention are the inert solvents which are customarily employed in organic chemistry and are known to those skilled in the art. Examples are, in particular: toluene, o-xylene, m-xylene, p-xylene, mesitylene, 2-chlorotoluene, 3-chlorotoluene, 4-chlorotoluene, monochlorobenzene, 1,2-dichlorobenzene, 1,3-dichlorobenzene, 1,4-dichlorobenzene, N-ethylcarbazole and mixtures thereof. Preferred solvents are toluene, xylene, monochlorobenzene and 1,2-dichlorobenzene, particularly preferably 1,2-dichlorobenzene. The inert solvents are preferably used in amounts of from 0.5 to 10 parts by weight, particularly preferably from 1 to 5 parts by weight, per part by weight of carbazole of the formula II.

In the catalysts of the formula IV, n is preferably an integer from 2 to 6, particularly preferably 3, and $R^2$, $R^3$, $R^4$ and $R^5$ are preferably hydrogen, methyl or ethyl, particularly preferably methyl. For example, it is possible to use ethylenediamine, 2-ethylaminoethylamine, 2-diethylaminoethylamine, 3-dimethylaminopropylamine, 3-diethylaminopropylamine, N,N,N',N'-tetramethylpropane-1,3-diamine, N,N-diethyl-N',N'-dimethylpropane-1,3-diamine, N,N,N',N'-tetramethylbutane-1,4-diamine, 1-diethylamino-4-aminopentane, N,N,N',N'-tetramethylhexane-1,6-diamine, N,N-dimethyidipropylenetriamine, bis(3-dimethylaminopropyl)amine, N,N,N',N'',N''-pentamethyldiethylenetriamine and N,N,N',N'',N''-pentamethyldipropylenetriamine. Particular preference is given to N,N-N',N'-tetramethylpropane-1,3-diamine and N,N-diethyl-N',N'-dimethylpropane-1,3-diamine and very particular preference is given to N,N,N',N'-tetramethylpropane-1,3-diamine.

The catalysts of the formula IV are preferably used in amounts of from 0.001 to 0.05 mol, particularly preferably from 0.005 to 0.02 mol, per mole of carbazole used. Compared to the closest prior art, these are significantly smaller amounts for achieving an equally high degree of conversion. This results in ecological and economic advantages. Furthermore, the use of the catalysts of the formula IV surprisingly makes it possible to omit an aftertreatment of the product phase with aqueous sulfuric acid, since after the phase separation the catalyst is present in the aqueous phase and at most traces are present in the organic product phase.

This simplified work-up gives a further economic advantage of the process of the invention compared to the prior art.

The process of the invention is preferably carried out at temperatures of from 70 to 160° C., particularly preferably from 80 to 130° C.

The process of the invention can be carried out, for example, by charging an autoclave with a carbazole of the formula II, inert solvent, aqueous alkali metal hydroxide and catalyst of the formula IV and, at a reaction temperature of 100° C. and a pressure of at most 5 bar, metering in ethyl chloride while stirring. The reaction mixture is subsequently stirred further for from 2 to 10 hours at 100° C. until the carbazole content, based on N-ethylcarbazole formed, is below a desired limit, for example <1% or <0.1%.

After the reaction is complete, inorganic salts which have precipitated are dissolved by means of water. The organic phase obtained after phase separation can, owing to the high yield of >95% of the theoretical yield of N-ethylcarbazole and the high purity, be used directly without further purification operations for subsequent reactions, for example nitrations.

The following examples illustrate the invention without restricting it. Contents indicated are in percent by weight.

EXAMPLE 1

A heatable Hastelloy autoclave having a capacity of 3 liters is charged with 502 g of carbazole (3.0 mol), 680 g of o-dichlorobenzene, 480 g of 50% strength sodium hydroxide solution (6.0 mol) and 4.4 g of N,N,N',N'-tetramethylpropane-1,3-diamine (0.034 mol). The autoclave is made inert with $N_2$, closed and heated to an internal temperature of 100° C. In a reservoir autoclave which is connected to the reaction autoclave via a capillary which can be closed off, 273 g of ethyl chloride (4.2 mol) are heated to an internal temperature of from 75 to 80° C., so that a pressure of at most 5 bar (all pressures given as gauge pressure) is built up. The ethyl chloride is then metered into the reaction autoclave at an internal temperature of 100° C. via a needle valve by means of the pressure difference at such a rate that the internal pressure in the reaction autoclave does not exceed 4 bar. The total addition time is 2 hours. After the addition, stirring is continued for another 4 hours at 100° C., the mixture is subsequently cooled while stirring to about 40° C. and the reaction mixture is then transferred from the autoclave into an aspirator. Residues of the reaction mixture are rinsed from the autoclave into the aspirator using 400 g of o-dichlorobenzene followed by 1000 g of water. The contents of the aspirator are vigorously stirred until the sodium chloride has completely dissolved in the aqueous phase and the contents are subsequently transferred to a separating funnel. After separating off the aqueous phase, 1670 g of a solution of N-ethylcarbazole in o-dichlorobenzene are obtained. According to analysis by gas chromatography, this solution contains 34.8% of N-ethylcarbazole, <0.1% of carbazole and <0.01% of N,N,N',N'-tetramethylpropane-1,3-diamine. Conversion is thus complete and the yield is 99.3% of theory.

COMPARATIVE EXAMPLE 1

The apparatus described in Example 1 is charged with 502 g of carbazole (3.0 mol), 680 g of o-dichlorobenzene, 480 g of 50% strength sodium hydroxide solution (6.0 mol) and 3.4 g of triethylamine (0.034 mol). Using a method similar to Example 1, 273 g of ethyl chloride (4.2 mol) are metered in. The total addition time is 6 hours. After the addition, the mixture is stirred further for 4 hours at 100° C., subsequently cooled to about 40° C. while stirring and the reaction mixture is transferred from the autoclave into an aspirator. Residues of the reaction mixture are rinsed from the autoclave into the aspirator using 400 g of o-dichlorobenzene followed by 1000 g of water. The contents of the aspirator are stirred vigorously until the sodium chloride has completely dissolved in the aqueous phase and the mixture is subsequently filtered. The filter cake is washed with 100 g of o-dichlorobenzene and sucked dry. The filtrate is transferred to a separating funnel. After separating off the aqueous phase, 1736 g of a solution of N-ethylcarbazole in o-dichlorobenzene are obtained. According to analysis by gas chromatography, this solution contains 31.1% of N-ethylcarbazole, 0.6% of carbazole and 0.08% of triethylamine. The filter cake weighs 28 g after drying and, according to thin layer chromatography, is pure carbazole. The conversion of the carbazole is thus only 92.3%.

EXAMPLE 2

502 g of carbazole (3.0 mol), 680 g of o-dichlorobenzene, 480 g of 50% strength sodium hydroxide solution (6.0 mol) and 20.6 g of N,N,N',N'-tetramethylhexane-1,6-diamine (0.12 mol) are placed in the apparatus described in Example 1 and 273 g of ethyl chloride (4.2 mol) are metered in over 2 hours. The mixture is stirred further for 3 hours at 100° C., subsequently cooled while stirring to about 40° C. and the reaction mixture is transferred from the autoclave into an aspirator. Residues of the reaction mixture are rinsed from the autoclave into the aspirator using 400 g of o-dichlorobenzene followed by 1000 g of water. The contents of the aspirator are stirred vigorously until the sodium chloride has completely dissolved in the aqueous phase and the mixture is subsequently transferred to a separating funnel. After separating off the aqueous phase, 1680 g of a solution of N-ethylcarbazole in o-dichlorobenzene are obtained. According to analysis by gas chromatography, this solution contains 34.7% of N-ethylcarbazole and <0.1% of carbazole. Conversion is thus complete and the yield is 99.6% of theory.

EXAMPLE 3

N-Ethylcarbazole is prepared as indicated in Example 2 with the only difference being that 13.9 g (0.12 mol) of N,N,N',N'-tetramethylethane-1,2-diamine are used in place of 20.6 g (0.12 mol) of N,N,N',N'-tetramethylhexane-1,6-diamine. This gives 1675 g of a solution of N-ethylcarbazole in o-dichlorobenzene. According to analysis by gas chromatography, this solution contains 34.5% of N-ethylcarbazole and <0.1% of carbazole. Conversion is thus complete and the yield is 98.8% of theory.

The following table shows further examples of N-alkylcarbazoles of the formula I which can be prepared in high yields by the process of the invention using the alkylating agents of the formula III shown in column 3 and the catalysts of the formula IV shown in column 4.

| Example | Carbazole of the formula II | Alkyl halide of the formula III | Catalyst of the formula IV |
|---|---|---|---|
| 4 | Carbazole | Methyl bromide | N,N,N',N'-Tetramethylpropane-1,3-diamine |
| 5 | Carbazole | Hexyl chloride | N,N,N',N'-Tetramethylpropane-1,3-diamine |
| 6 | Carbazole | Ethyl chloride | N,N-Diethylpropane-1,3-diamine |
| 7 | 2-Methylcarbazole | Ethyl chloride | N,N,N',N'-Tetramethylpropane-1,3-diamine |
| 8 | 1-Methoxycarbazole | Ethyl chloride | N,N,N',N'-Tetramethylpropane-1,3-diamine |
| 9 | 3-Chlorocarbazole | Ethyl chloride | N,N,N',N'-Tetramethylpropane-1,3-diamine |
| 10 | 3-Nitrocarbazole | Ethyl chloride | N,N,N',N'-Tetramethylpropane-1,3-diamine |

We claim:

1. A process for preparing N-alkylcarbazoles of the formula I

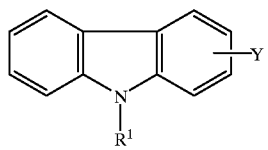

(I)

where $R^1$ is $(C_1-C_6)$-alkyl and

Y is hydrogen, $(C_1-C_6)$-alkyl, $(C_1-C_6)$-alkoxy, nitro or halogen, by reacting a carbazole of the formula II

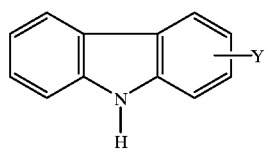

(II)

with an alkyl halide of the formula III $R^1-X$        III where X is a halogen atom,
in an inert solvent in the presence of an inorganic base and a catalyst of the formula IV $R^2R^3N-(CH_2)_n-NR^4R^5$        IV where n is an integer from 2 to 8, $R^2$, $R^3$ and $R^4$ are, independently of one another, hydrogen or $(C_1-C_4)$-alkyl and $R^5$ is hydrogen, $(C_1-C_4)$-alkyl, amino-$(C_1-C_4)$-alkyl or N,N-di$(C_1-C_4)$-alkylamino-$(C_1-C_4)$-alkyl.

2. The process as claimed in claim 1, wherein, in the compound of the formula I, $R^1$ is methyl or ethyl and Y is hydrogen.

3. The process as claimed in claim 1, wherein the alkyl halide of the formula III is methyl chloride, methyl bromide, methyl iodide, ethyl chloride, ethyl bromide, n-propyl chloride, n-propyl bromide, iso-butyl chloride, iso-butyl bromide, n-pentyl chloride or n-hexyl chloride.

4. The process as claimed in claim 1, wherein the alkyl halide of the formula III is used in an amount of from 1.0 to 1.8 mol per mole of carbazole of the formula II.

5. The process as claimed in claim 1, wherein the alkyl halide of the formula III is used in an amount of from 1.1 to 1.5 mol per mole of carbazole of the formula II.

6. The process as claimed in claim 1, wherein the inorganic base is an alkali metal alkoxide, hydroxide, oxide or carbonate, or a tertiary phosphate of an alkali metal or alkaline earth metal or a mixture thereof.

7. The process as claimed in claim 1, wherein the inorganic base is used in an amount of from 0.9 to 3.0 eq per mole of carbazole of the formula II.

8. The process as claimed in claim 1, wherein the inorganic base is used in an amount of from 1.1 to 2.0 eq per mole of carbazole of the formula II.

9. The process as claimed in claim 1, wherein the inert solvent is toluene, o-xylene, m-xylene, p-xylene, mesitylene, 2-chlorotoluene, 3-chlorotoluene, 4-chlorotoluene, monochlorobenzene, 1,2-dichlorobenzene, 1,3-dichlorobenzene, 1,4-dichlorobenzene, N-ethylcarbazole or a mixture thereof.

10. The process as claimed in claim 1, wherein, in the catalyst of the formula IV, n is an integer from 2 to 6 and $R^2$, $R^3$, $R^4$ and $R^5$ are hydrogen, methyl or ethyl.

11. The process as claimed in claim 1, wherein, in the catalyst of the formula IV, n is 3.

12. The process as claimed in claim 1, wherein the catalyst of the formula IV is ethylenediamine, 2-ethylaminoethylamine, 2-diethylaminoethylamine, 3-dimethylaminopropylamine, 3-diethylaminopropylamine, N,N,N',N'-tetramethylpropane-1,3-diamine, N,N-diethyl-N',N'-dimethylpropane-1,3-diamine, N,N,N',N'-tetramethylbutane-1,4-diamine, 1-diethylamino4-aminopentane, N,N,N',N'-tetramethylhexane-1,6-diamine, N,N-dimethyidipropylenetriamine, bis(3-dimethylaminopropyl)amine, N,N,N',N",N"-pentamethyldiethylenetriamine or N,N,N',N",N"-pentamethyldipropylenetriamine.

13. The process as claimed in claim 1, wherein the catalyst of the formula IV is used in an amount of from 0.001 to 0.05 mol per mole of carbazole used.

14. The process as claimed in claim 1, wherein the catalyst of the formula IV is used in an amount of from 0.005 to 0.02 mol per mole of carbazole used.

* * * * *